United States Patent
Wang et al.

(10) Patent No.: US 9,296,670 B2
(45) Date of Patent: Mar. 29, 2016

(54) PROCESS FOR THE MANUFACTURE OF 2,3,3,3-TETRAFLUOROPROPENE

(71) Applicant: Honeywell International, Inc., Morristown, NJ (US)

(72) Inventors: Haiyou Wang, Amherst, NY (US); Hsueh S. Tung, Getzville, NY (US); Haluk Kopkalli, Staten Island, NY (US); Yuon Chiu, Denville, NJ (US); Gustavo Cerri, Parsippany, NJ (US); Jeffrey Ball, Morisstown, NJ (US); Philip L. Da Prato, Annandale, NJ (US); Xuehui Sun, Kennet Square, PA (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/377,727

(22) PCT Filed: Feb. 8, 2013

(86) PCT No.: PCT/US2013/025299
§ 371 (c)(1),
(2) Date: Aug. 8, 2014

(87) PCT Pub. No.: WO2013/119919
PCT Pub. Date: Aug. 15, 2013

(65) Prior Publication Data
US 2015/0005536 A1    Jan. 1, 2015

Related U.S. Application Data

(60) Provisional application No. 61/597,671, filed on Feb. 10, 2012.

(51) Int. Cl.
| | |
|---|---|
| C07C 17/23 | (2006.01) |
| C07C 17/395 | (2006.01) |
| C07C 17/06 | (2006.01) |
| C07C 17/087 | (2006.01) |
| C07C 17/25 | (2006.01) |
| C07C 17/386 | (2006.01) |
| C07C 17/389 | (2006.01) |
| B01J 27/08 | (2006.01) |

(52) U.S. Cl.
CPC .............. *C07C 17/395* (2013.01); *B01J 27/08* (2013.01); *C07C 17/06* (2013.01); *C07C 17/087* (2013.01); *C07C 17/23* (2013.01); *C07C 17/25* (2013.01); *C07C 17/386* (2013.01); *C07C 17/389* (2013.01); *Y02P 20/582* (2015.11)

(58) Field of Classification Search
CPC .... C07C 17/395; C07C 17/23; C07C 17/386; C07C 17/06; C07C 17/25; C07C 17/087; C07C 17/389; B01J 27/08

USPC ................................................ 570/156, 179
See application file for complete search history.

(56) References Cited

U.S. PATENT DOCUMENTS

| | | | |
|---|---|---|---|
| 2,931,840 | A | 4/1960 | Marquis |
| 4,906,796 | A | 3/1990 | Yates |
| 5,233,107 | A | 8/1993 | Jansen |
| 5,336,377 | A | 8/1994 | Yates et al. |
| 5,944,962 | A | 8/1999 | Boyce |
| 7,205,444 | B1 | 4/2007 | Chiu et al. |
| 7,795,480 | B2 | 9/2010 | Merkel et al. |
| 7,803,283 | B2 | 9/2010 | Pham et al. |
| 8,034,251 | B2 | 10/2011 | Merkel et al. |
| 8,053,612 | B2 | 11/2011 | Wang et al. |
| 8,058,486 | B2 | 11/2011 | Merkel et al. |
| 8,084,653 | B2 | 12/2011 | Tung et al. |
| 2007/0197841 | A1 | 8/2007 | Mukhopadhyay et al. |
| 2009/0124837 | A1 | 5/2009 | Mukhopadhyay et al. |
| 2009/0203945 | A1 | 8/2009 | Mukhopadhyay et al. |
| 2009/0240090 | A1 | 9/2009 | Merkel et al. |
| 2009/0256110 | A1 | 10/2009 | Merkel et al. |
| 2009/0287026 | A1 | 11/2009 | Kopkalli et al. |
| 2010/0036179 | A1 | 2/2010 | Merkel et al. |
| 2010/0048961 | A1 | 2/2010 | Merkel et al. |
| 2010/0137658 | A1 | 6/2010 | Merkel et al. |
| 2010/0187088 | A1 | 7/2010 | Merkel et al. |
| 2010/0331583 | A1 | 12/2010 | Johnson et al. |
| 2011/0105807 | A1 | 5/2011 | Kopkalli et al. |
| 2012/0053371 | A1 | 3/2012 | Johnson et al. |
| 2012/0129687 | A1 | 5/2012 | Wang et al. |
| 2012/0149951 | A1 | 6/2012 | Mukhopadhyay et al. |

FOREIGN PATENT DOCUMENTS

| | | |
|---|---|---|
| CN | 102001910 A | 4/2011 |
| EP | 2 108 638 A1 | 10/2009 |
| EP | 2 119 692 A1 | 11/2009 |

(Continued)

OTHER PUBLICATIONS

International Search Report issued in PCT/US2013/025299 dated May 10, 2013.

(Continued)

*Primary Examiner* — Shailendra Kumar
(74) *Attorney, Agent, or Firm* — Scully Scott Murphy and Presser (57) ABSTRACT

A method for forming 2,3,3,3-tetrafluoropropene (HFO-1234yf) comprising providing a dehydrochlorination starting material having relatively low concentrations of 2-chloro-3,3,3-trifluoropropene (HCFO-1233xf), especially and preferable less than about 8.0% when the dehydrochlorination reaction utilizes no substantial amount of catalyst or catalyst comprising austenitic nickel-based materials.

26 Claims, 1 Drawing Sheet

(56) References Cited

FOREIGN PATENT DOCUMENTS

| WO | WO 2011/110889 A1 | 9/2011 |
| WO | 2012067980 A2 | 5/2012 |
| WO | 2013049105 A1 | 4/2013 |

OTHER PUBLICATIONS

Banks, R.E. et al., Preparation of 2,3,3,3-tetrafluoropropene from trifluoroacetylacetone and sulphur tetrafluoride, Journal of Fluorine Chemistry, (1997), vol. 82, pp. 171-174.

Supplementary European Search Report issued in Application No. EP 13 75 6215, mailed Aug. 19, 2015.

US 9,296,670 B2

PROCESS FOR THE MANUFACTURE OF 2,3,3,3-TETRAFLUOROPROPENE

RELATED APPLICATIONS

This application is a '371 of PCT Application No. PCT/US2013/025299, which was filed on Feb. 8, 2013 and claims priority of U.S. Ser. No. 61/597,672, filed in the United States Patent Office on Feb. 10, 2012, the contents of both of which are incorporated by reference.

FIELD OF INVENTION

This invention relates to a process for preparing fluorinated organic compounds, more particularly to a process for preparing fluorinated olefins, and even more particularly to a process for preparing 2,3,3,3-tetrafluoropropene (HFO-1234yf).

BACKGROUND OF THE INVENTION

Certain hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike most chlorofluorocarbons (CFCs) and hydrochlorofluorocarbons (HCFCs), most HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf is a leader among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is potentially hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding the above-noted process and other processes for producing fluorinated olefins in general and fluorinated propenes in particular, it was appreciated that a need remains for a more economically efficient means of producing hydrofluoroolefins in general and hydrofluoropropenes in particular, such as HFO-1234yf. The present invention satisfies this need among others.

SUMMARY

One aspect of the present invention provides a method for forming 2,3 3,3-tetrafluoropropene (HFO-1234yf) comprising providing a dehydrochlorination starting material having relatively low concentrations of 2-chloro-3,3,3-trifluoropropene (HCFO-1233xf) and dehydrochlorinating said starting material in the presence of a metal alloy. Not wishing to be bound by or to any particular theory of operation, certain aspects of the present invention are based on the observation and understanding that, during certain dehydrochlorination reactions of certain dehydrochlorination starting materials, such as 2-chloro-1,1,1,2-tetrafluoropropane (HCFC-244bb), to produce 2,3,3,3-tetrafluoropropene (HFO-1234yf), the presence of 2-chloro-3,3,3-trifluoropropene (HCFO-1233xf) in the reaction starting materials, such as HCFC-244bb feedstock, can lead to dramatically reduced conversion of HCFC-244bb to HFO-1234yf and increased formation of 3,3,3-trifluoropropyne ($CF_3CCH$), which is the dehydrochlorinated product of 2-chloro-3,3,3-trifluoropropene (HCFO-1233xf). In addition, the 2-chloro-3,3,3-trifluoropropene copresent in the starting material, when subjected to dehydrochlorination, can lead to the formation of oligomers, which can produce tar. This result is not only disadvantageous from the standpoint of a reduced yield of the desired product, it is additionally disadvantageous because the 3,3,3-trifluoropropyne ($CF_3CCH$) byproduct is a flammable gas and toxic, and thus undesired. Accordingly, the present invention relates, in part, to methods of improving the conversion of dehydrochlorination starting materials, such as HCFC-244bb, in certain dehydrochlorination reactions and of reducing the amount of unwanted reaction by-products, such as $CF_3CCH$, by substantially reducing and/or substantially eliminating the presence of HCFO-1233xf in the reactor feed, especially in the HCFC-244bb feed stream.

In one aspect, the present invention relates to a feedstock for use in preparing a fluoroolefin, especially in dehydrochlorination reactions, which are described hereinbelow. In one embodiment, the dehydrochlorination reaction occurs in the presence of a metal alloy, and in another embodiment, using a nickel metal alloy. In another embodiment, the dehydrochlorination reaction is conducted without the use of cesium chloride based catalyst. In other embodiments, the reaction occurs within a reactor comprised of metal alloy. In another aspect of the present invention, the reaction is conducted in a reactor comprised of nickel metal alloy, and in another embodiment, the reactor is comprised of austenitic nickel-based material(s) such as Inconel 625. In other aspects of such embodiments, the reaction is carried out using any of the embodiments described above, such as a reactor comprised of austenitic nickel-based material(s) such as Inconel 625 and in the substantial absence of added CsCl-based catalytic material or particles, and in certain embodiments in the substantial absence of any added catalytic material or particles. For all of such embodiments, the feedstock or feed stream to the reactor has less than about 20% by weight of 2-chloro-3,3,3-trifluoropropene. In another embodiment, the feedstock or feedstream contains less than about 8.0% by weight of HCFO-1233xf (as defined hereinafter), while in other embodiments, it contains less than about 2% by weight of HCFO-1233xf and in some other embodiments less than about 1% by weight of HCFO-1233xf. In another embodiment, the feedstream or feedstock comprises 2-chloro-1,1,1,2-tetrafluoropropane, which is substantially free of HCFO-1233xf. In an aspect of the present invention, the feedstock or organic feed stream comprises in major proportion HCFC-244bb that is substantially pure or sufficiently so pure that the presence of HCFO-1233xf in the composition cannot be detected by any instrument.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

As used herein, the term "weight %" with respect to the amount of HCFO-1233xf in a feed stream or in feedstock, means the weight percent of the HCFO-1233xf based on the total of the organic portion of the dehydrochlorination reactant and 1233xf in the feed to the reactor.

As used herein, the term "substantially free" means that means less than about 0.3% by weight.

In embodiments of the present invention, especially those embodiments comprising dehydrochlorination reactions, HCFO-1233xf is present in the reaction material in an amount less than about 20 wt %. In another embodiment, the HCFO-1233xf is present in less than 15 wt %, while in another aspect, it is present in less than about 10 wt %. In another aspect of the present invention, it is present in less than about 8 wt %. In certain embodiments, the HCFO-1233xf is present in the reaction material in an amount less than about 5 wt %, and in another embodiment, less than about 2.5 wt %, and in another embodiment, less than about 1.0 wt %. In certain embodiments, the feed material is substantially free of HCFO-1233xf.

In another aspect, the present invention relates to a method for reducing the level of HCFO-1233xf within a dehydrochlorination reaction feed, such as a HCFC-244bb feedstock, by providing a composition comprising dehydrochlorination reaction feed material, e.g., HCFC-244bb, containing HCFO-1233xf, and reducing the level of HCFO-1233xf such that the amount of HCFO-1233xf present comprises less than about −20% by weight, in one embodiment, less than 15 wt % in another, less than about 10 wt %, less than about at 8 wt. % in another, still further less than about 5 wt % by weight; less than about 2.5% and in another embodiment, less than about 1 wt %.

In another aspect of the present invention, the dehydrochlorination reaction feed material is substantially free of HCFO-1233xf. As described herein, the dehydrochlorination reaction may be conducted in the liquid phase or vapor phase using the feedstock or feedstream described herein. In one embodiment, the dehydrochlorination reaction utilizes no substantial amount of catalyst or catalyst comprising austenitic nickel-based materials. While the method of reducing the level of HCFO-1233xf may include any one or combination of the methods provided herein, in certain aspects the methods include one or any combination of the following:

(i) distilling the composition to separate HCFO-1233xf from dehydrochlorination reaction feed, such as HCFC-244bb. In certain embodiments, the distillation method may include extractive distillation where HCFO-1233xf or HCFC-244bb is extracted using an extracting agent or solvent in a sufficient volume to change the volatility of 2-chloro-3,3,3-trifluoropropene and/or 2-chloro-1,1,1,2-tetrafluoropropane. The composition is then distilled to provide 2-chloro-1,1,1,2-tetrafluoropropane as a distillate. Such agents or solvents may include, but are not limited to, trans-HCFO-1233zd, cis-HCFO-1233zd, HCFO-1223 isomers, and HCFO-1232 isomers and combinations thereof;

(ii) treating the starting composition with excess HF to convert unreacted HCFO-1233xf into HCFC-244bb in the presence of a catalyst in a post-catalysis reactor. In certain aspects, the composition is treated with excess HF at a temperature between about 70° C. and about 120° C. and/or a pressure between about 50 psig and about 120 psig.

(iii) treating the starting composition using azeotropic distillation. In certain embodiments such treatment includes adding a third component to the composition in an effective amount to form a ternary azeotrope with HCFO-1233xf, and the dehydrochlorination reaction feed, such as HCFC-244bb and/or a binary azeotrope with one or both HCFO-1233xf and the dehydrochlorination reaction feed, such as HCFC-244bb. The azeotropes are then removed from the composition using standard separation techniques, such as, but not limited to, distillation;

(iv) photochlorinating the starting composition to saturate the HCFO-1233xf and form 1,2,2-trichloro-3,3,3-trifluoropropane (HCFC-233ab). In certain embodiments, the photochlorination treatment includes exposing the composition to radiation (e.g. ultraviolet light) in the presence of at least one chlorination agent. HCFC-233ab is then removed from the composition using standard methods, such as, but not limited to, distillation;

(v) cooling the starting composition to a temperature where one of 2-chloro-1,1,1,2-tetrafluoropropane and 2-chloro-3,3,3-trifluoropropene forms a solid and the other remains a liquid. In certain embodiments, the composition is cooled to a temperature where 2-chloro-1,1,1,2-tetrafluoropropane forms a solid and 2-chloro-3,3,3-trifluoropropene is a liquid. 2-chloro-1,1,1,2- tetrafluoropropane is then removed. In certain embodiments, the composition is cooled to a temperature between about −75° C. and −85° C.

(vi) passing the starting composition over a fixed bed of solid adsorbents selected from activated carbons and zeolites and/or molecular sieves, wherein the pores in the zeolites and/or molecular sieves are sized to filter 2-chloro-1,1,1,2-tetrafluoropropane from 2-chloro-3,3, 3-trifluoropropene. In certain aspects, the pores are between about 3 Å to about 10 Å;

(vii) separating HCFO-1233xf from dehydrochlorination reaction feed, such as HCFC-244bb, by chromatography, where a mixture of HCFO-1233xf and HCFC-244bb are fed through a column containing a stationary substrate; and (viii) mixing said starting composition with liquid hydrofluoric acid to form a mixture comprised of 2-chloro-1, 1,1,2-tetrafluoropropane, 2-chloro-3,3,3-tri-fluoropropene and HF, said HF present in less than about 10% by weight of the starting composition and distilling the resulting mixture in a reboiler and collecting the product substantially free of HCFO-1233xf and purer in 2-chloro-1,1,1,2-tetrafluoropropane then in the resulting starting mixture.

In further embodiments, the present invention relates to a process for preparing HFO-1234yf, which is substantially free of 3,3,3-trifluoropropyne by providing a starting composition including HCFC-244bb that is substantially free of HCFO-1233xf and contacting said starting composition with a dehydrochlorination catalyst to produce a final composition comprising HFO-1234yf, which is substantially free of 3,3, 3-trifluoropropyne.

In certain embodiments, the dehydrochlorination catalyst is selected from the group consisting of (i) one or more metal halides, (ii) one or more halogenated metal oxides, (iii) one or more zero-valent metals/metal alloys, (iv) austenitic nickel-based materials (such as Inconel 625) and (v) a combination of two or more of these. In certain embodiments, the dehydrochlorination catalyst does not comprise predominately, and even more preferably does not contain any substantial amount of cesium chloride (CsCl) based catalyst together with a magnesium fluoride ($MgF_2$) based catalyst.

In another embodiment, the present invention is directed to the process of preparing 2,3,3,3-tetrafluoropropene that is substantially free of 3,3,3-trifluoropropyne comprising:

(i) providing a starting composition comprising a 2-chloro-1,1,1,2-tetrafluoropropane that is substantially free of 2-chloro-3,3,3-trifluoropropene; and (ii) contacting said starting composition with a dehydrochlorination catalyst to produce a final composition comprising 2,3,3,3-tetrafluoropropene, said final composition being substantially free of 3,3,3-trifluoropropyne.

In an embodiment, the process of preparing 2,3,3,3-tetrafluoropropene additionally comprises measuring the amount of 3,3,3-trifluoropropyne present in the final composition.

In even further aspects, the present invention relates to a process for preparing 2,3,3,3-tetrafluoropropene by:

(i) providing a starting composition including a compound of Formulas I, II, or III:|

$CX_2=CCl—CH_2X$                                                                      (I);

$CX_3—CCl=CH_2$                                                                     (II); or $CX_3—CHCl—CH_2X$                                                 (III)

wherein X is independently selected from F, Cl, Br, and I, provided that at least one X is not fluorine;

(ii) contacting the starting composition with a first fluorinating agent to produce a first intermediate composition including HCFO-1233xf and a first chlorine-containing byproduct;

(iii) contacting the first intermediate composition with a second fluorinating agent to produce a second intermediate composition including HCFC-244bb and HCFO-1233xf;

(iv) reducing the level of HCFO-1233xf in the second intermediate composition to produce a third intermediate composition including HCFC-244bb that is substantially free of HCFO-1233xf; and (v) dehydrochlorinating at least a portion of the HCFC-244bb to produce a reaction product including HFO-1234yf that is substantially free of 3,3,3-trifluoropropene.

Additional embodiments and advantages to the present invention will be readily apparent to one of skill in the art, based on the disclosure provided herein.

DETAILED DESCRIPTION OF PREFERRED EMBODIMENTS

According to one embodiment, the present invention relates to a manufacturing process for making HFO-1234yf using a starting or intermediate material comprising HCFC-244b that is substantially free of HCFO-1233xf. The inventors have surprisingly found that the presence of HCFO-1233xf decreases conversion of HCFC-244bb to HFO-1234yf, which results in larger recycle, increased equipment costs, and higher operating costs. In addition, the presence of HCFO-1233xf increases the formation of 3,3,3-trifluoropropyne ($CF_3CCH$), which is a flammable gas and thus undesired. Its removal from the final product, namely HFO-1234yf, will incur extra cost and possibly yield loss as well. For example, using distillation to bring down $CF_3CCH$ level from 50-100 ppm to 5-12 ppm caused an HFO-1234yf loss of almost 10%. Accordingly, the present invention provides methods of removing HCFO-1233xf from the reactor feed to improve the overall efficiency of the HFO-1234yf conversion process.

In certain aspects, the preparation of HFO-1234yf generally includes at least three reaction steps, as follows:

(i) ($CX_2=CCl—CH_2X$ or $CX_3—CCl=CH_2$ or $CX_3—CHCl—CH_2X$)+HF→2-chloro-3,3,3-trifluoropropene (HCFO-1233xf)+HCl in a vapor phase reactor charged with a solid catalyst;

(ii) 2-chloro-3,3,3-trifluoropropene (HCFO-1233xf)+HF→2-chloro-1,1,1,2-tetrafluoropropane (HCFC-244bb) in a liquid phase reactor charged with a liquid hydrofluorination catalyst; and (iii) 2-chloro-1,1,1,2-tetrafluoropropane (HCFC-244bb)→2,3,3,3-tetrafluoropropene (HFO-1234yf) in a vapor phase reactor.

wherein X is independently selected from F, Cl, Br, and I, provided that at least one X is not fluorine.

Generally speaking, the starting material of the first reaction step may be represented by one or more chlorinated compounds according to Formulas I, II, and/or III:

$$CX_2\!\!=\!\!CCl\!-\!CH_2X \qquad \text{(Formula I)}$$

$$CX_3\!-\!CCl\!\!=\!\!CH_2 \qquad \text{(Formula II)}$$

$$CX_3\!-\!CHCl\!-\!CH_2X \qquad \text{(Formula III)}$$

wherein X is independently selected from F, Cl, Br, and I, provided that at least one X is not fluorine. In certain embodiments, these compounds contain at least one chlorine, a majority of X is chlorine, or all X is chlorine.

In the first step, such starting materials (which, in certain embodiments includes 1,1,2,3-tetrachloropropene (1230xa) and/or 1,1,1,2,3-pentachloropropane (HCC-240 db)) is reacted with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, heavy intermediates, HCFC-244bb, HFC-245cb (1,1,1,2,2-pentafluoropropane), or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction, as described above, but may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuously, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

The effluent from the reactor may be optionally processed to achieve desired degrees of separation and/or other processing. By way of non-limiting example, the product effluent may contain one or more impurities, such as, HCl, unconverted reactants, and/or other by-products. These products may be removed using standard methods known or otherwise discussed herein. HCl, for example, can be recovered by conventional distillation, or using water or caustic scrubbers, as discussed in greater detail below, and the unreacted starting reagents isolated and recycled.

In the second step of the process for forming 2,3,3,3-tetrafluoropropene, HCFO-1233xf is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reactor can either be non-catalytic or it can contain a catalyst that can catalytically dehydrochlorinate HCFC-244bb to make HFO-1234yf.

The catalysts, if present, may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and I⁻. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Incoloy 825, Alloy 20, Hastelloy, Inconel 600, and Inconel 625.

In an aspect of the present invention, catalysts include activated carbon, stainless steel (e.g., SS 316), austenitic nickel-based alloys (e.g., Inconel 625), nickel, and in certain embodiments fluorinated 10% CsCl/MgO. A suitable reaction temperature is about 300-550° C. and a suitable reaction pressure may be between about 0-150 psig. The reactor effluent may be fed to a caustic scrubber or to a distillation column to remove the byproduct of HCl to produce an acid-free organic product which, optionally, may undergo further purification using one or any combination of purification techniques that are known in the art.

The reaction may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

In general, the effluent from the dehydrochlorination reactor may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used, HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

The inventors have surprisingly discovered that, during the dehydrochlorination of dehydrochlorination reactants, such as HCFC-244bb, to form HFO-1234yf, the presence of HCFO-1233xf in the feedstock decreases the conversion of the reactant, such as HCFC-244bb, to HFO-1234yf and increases the formation of 3,3,3-trifluoropropyne, an undesired by-product. Consequences of the lower conversion include a higher volume of reagent recycle, greater equipment use per reaction, and overall higher operating costs. Consequences of the formation of trifluoropropyne include extra cost and yield loss of 1234yf incurred in its removal. The present invention provides a solution to at least these problems by reducing the content of HCFO-1233xf in the feed stream, thereby improving HFO-1234yf production efficiency. To this end, and prior to the third reaction step, the feedstock composition, in one embodiment comprises and, in another embodiment, consisting essentially of HCFC-244bb, and is preferably first purified to form a feedstock that contains less than about 20% by weight of HCFO-1233xf. In another embodiment, the feed stream contains less than about 8.0 wt % of HCFO-1233xf. In still another embodiment, the feed stream is substantially free of HCFO-1233xf. In one aspect, HCFO-1233xf is provided in the purified feedstock of HCFC-244bb in an amount less than about 20.0 wt %, less than about 15.0 wt %, less than about 10.0 wt %, less than about 8.0 wt %, less than about 5.0 wt %, less than about 2.5 wt %, less than about 1.0 wt %. In another embodiment, the feed stream for the dehydrochlorination step is substantially free of HCFO-1233xf. In other embodiments, the feedstock for the dehydrochlorination reaction is comprised of 2-chloro-1,1,1,2-tetrafluoropropane and 2-chloro-3,3,3-trifluoropropene wherein the concentration of the 2-chloro-3,3,3-trichloropropene is 20% or 19% or 18% or 17% or 16% or 15% or 14% or 13% or 12% or 11% or 19% or 9% or 8% or 7% or 6% or 5% or 4% or 3% or 2% or 1% or 0.9% or 0.8% or 0.7% or 0.6% or 0.5% or 0.4% or 0.3% by weight. In another embodiment, the feedstock for the dehydrochlorination comprises 2-chloro-1,1,1,2-tetrafluoropropane substantially free of 2-chloro-3,3,3-trichloropropene. In an aspect of the present invention, the feedstock solution is comprised of at least about 80 wt % of 2-chloro-1,1,1,2-tetrafluoropropane and in another embodiment, it is at least about 85 wt % of 2-chloro-1,1,1,2-tetrafluoropropane, and in another embodiment, it is at least about 90 wt % of 2-chloro-1,1,1,2-tetrafluoropropane, while in another embodiment, it comprises at least about 92 wt % of 2-chloro-1,1,1,2-tetrafluoropropane, while still in another embodiment, at least about 95 wt % of 2-chloro-1,1,1,2-tetrafluoropropane. In still another embodiment, the feedstock comprises at least about 97.5 wt % of 2-chloro-1,1,1,2-tetrafluoropropane, and in another embodiment, at least about 99 wt % of 2-chloro-1,1,1,2-tetrafluoropropane and in still another embodiment, at least about 99.7 wt % of 2-chloro-1,1,1,2-tetrafluoropropane. In still another embodiment, the feedstock is comprised of the following embodiments: 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt % 94 wt %, 95 wt % 96 wt %, 97 wt %, 98 wt % 99 wt %, 99.1 wt %, 99.2 wt %, 99.3 wt %, 99.4 wt %, 99.5 wt %, 99.6 wt %, 99.7 wt % or higher of 2-chloro-1,1,1,2-tetrafluoropropane.

Such compositions, in certain aspects, improve conversion of HCFC-244bb to HFO-1234yf to least 20% or higher in one embodiment, 25% or higher in another embodiment, 30% or higher, in still another embodiment or 35% or higher, in another aspect of the invention. In addition, reduce the formation of $CF_3CCH$ in the dehydrochlorination reaction to at least 1000 ppm or lower in one embodiment, 500 ppm or lower in another embodiment, 400 ppm or lower in a third embodiment, 300 ppm or lower, in another embodiment or 200 ppm or lower in still another embodiment. Conversion and/or selectivity may be calculated by number of moles of product (HFO-1234yf) formed divided by number of moles of reactant consumed or, otherwise, using standard methods known in the art.

Any technique known in the art can be used to purify the dehydrochlorination reaction feed, such as HCFC-244bb, or otherwise remove HCFO-1233xf. The following separation methods are provided as embodiments of such purification methods, but are not necessarily limiting to the invention. Such embodiments may be performed alone, in any combination, and/or using one or more alternative separation methods otherwise known in the art.

In one embodiment, HCFO-1233xf may be separated from the HCFC-244bb stream using distillation and/or extractive distillation. Distillation, as is understood in the art, is a separation of HCFC-244bb from HCFO-1233xf based upon the differences in volatilities between the two compounds. In the present invention, such techniques may be performed using standard methods based upon the boiling temperatures of the ingredients, the surrounding pressure, and the like.

Extractive distillation refers to the separation of one of HCFO-1233xf or HCFC-244bb from the other using an extracting agent or solvent. As set forth in U.S. Pat. No. 7,803,283, the contents of which are incorporated herein by reference, HCFO-1233xf and HCFC-244bb are known in the art to exhibit azeotropic properties when provided together in certain component amounts. To separate one component from the other, an extracting agent may be added to such a solution. As used herein, the term "extracting agent" refers to a compound or mixture of compounds that alters the volatility of one or both of HCFO-1233xf and HCFC-244bb to allow for separation of these compounds using standard means, e.g. distillation. Preferably, though not exclusively, such agents have a low volatility and do not form secondary azeotrope or azeotrope-like compositions with either or both of HCFO-1233xf and HCFC-244bb. By way of non-limiting example, in one embodiment, the extracting agent is added to the mixture of HCFO-1233xf and HCFC-244bb at a high concentration. The composition is distilled and one of either HCFO-1233xf or HCFC-244bb is then withdrawn from the mixture as distillate. The bottoms product, which includes the remaining component and the extracting agent is isolated and optionally purified to the extent necessary or desirable. In certain embodiments of the present invention, the extracting agent may be any agent that facilitates the isolation of HCFC-244bb as the distillate. To this end, HCFC-244bb is isolated/separated as the distillate and then processed for conversion to HFO-1234yf. HCFO-1233xf is optionally purified from the bottom stream and may be recycled for conversion to HCFC-244bb. Extracting agents that are useful in accordance with the present invention, particularly for purification of HCFC-244bb in the distillate include, but are not limited to, trans-HCFO-1233zd, cis-HCFO-1233zd, HCFO-1223 isomers, and HCFO-1232 isomers.

In another embodiment, the stream may be treated in a post-catalysis reactor with excess HF until it is substantially free of any unreacted HCFO-1233xf. In certain non-limiting embodiments, for example, the HCFC-244bb effluent may be treated in a vapor phase catalytic reactor such that the excess HCFO-1233xf is further converted to HCFC-244bb. Such a reaction may proceed under mild conditions than would typically be used. To this end, the post-catalysis reaction may be provided under temperature and pressure conditions less than typically used in a vapor reaction. Such conditions have been shown to be more ideal for achieving near complete conversion of the post-reaction effluent. In one embodiment, the post-catalysis reaction proceeds at a temperature between about 70° C. and about 120° C., or in certain embodiments around 100° C. It may also proceed at a pressure between about 50 psig and about 120 psig or around 90 psig. Additional HF is not necessarily required for the reaction to proceed, but rather, the excess HF provided in the initial reaction may be used. Additional HF, however, may be injected into the reactor to the extent necessary to complete the conversion. Any catalyst suitable for the fluorination of HCFO-1233xf to HCFC-244bb is acceptable. Such catalysts may include antimony pentachloride or antimony fluoride supported on activated carbon or, one or more of the catalysts identified herein, or otherwise known in the art.

In a further aspect, HCFO-1233xf may be removed from the HCFC-244bb feedstream using azeotropic distillation. To this end, a third component, such as but not limited to, HF, may be provided to form an azeotrope or azeotropic composition, which is then isolated from the composition. More specifically, the addition of the third component forms a ternary azeotrope and/or binary azeotropes with HCFO-1233xf and/or HCFC-244bb. These azeotropes may be separated from the solution using standard separation means, such as distillation, such that a portion of the HCFC-244bb remains in solution. This portion is then isolated as purified HCFC-244bb that is substantially free of HCFO-1233xf. Such azeotropes and methods of azeotropic separation or distillation may further include those disclosed in U.S. Pat. No. 7,803,283, and U.S. Published Application Nos. 2010/0187088 and 2009/0256110, the contents each of which are incorporated herein by reference.

In an alternative embodiment, the HCFC-244bb product stream is photochlorinated to saturate the HCFO-1233xf and form HCFC-233ab (1,2,2-trichloro-3,3,3-trifluoropropane), which then may be removed from the solution. In certain embodiments, the photochlorination reaction includes exposing the HCFC-244bb feed stream to radiation in the presence of a chlorination reagent. While not limited thereto, in certain aspects, the radiation is in the ultraviolet range, preferably in the range of from about 200 to about 400 nm. The chlorination agent may include chlorine gas, either neat or with a diluent such as nitrogen. The chlorine is reacted with the HCFO-1233xf in the presence of UV light so that the chlorine is added across the double bond. The reaction is preferably carried out in the vapor phase at temperature of from about −20° C. to about 200° C., and even more preferably from about 0° C. to about 100° C. for a time of from about 5 seconds to about 5 hours, more preferably from about 15 seconds to about 30 min. The reaction product, e.g. HCFC-233ab, has an altered boiling point, thus it may then be subjected to one or more separation steps, such as distillation, to remove it from the HCFC-244bb feed. The foregoing embodiment exemplifying a vapor phase photochlorination reaction is not necessarily limiting to the invention. To this end, the foregoing reaction may also be adapted to be performed in the liquid phase using standard procedures known in the art. In liquid phase reactions, it is desirable to maintain a reaction temperature below the boiling point of the 1233xf/244bb mixture. To this end, the pressure or temperature of the reaction may be adjusted such that the reaction mixture remains, at least in part, in the liquid phase. Examples of the foregoing vapor and liquid phase reactions and reaction conditions are provided in U.S. Pat. Nos. 7,205,444 and 5,336,377, the contents of which are incorporated herein by reference.

In even further embodiments, HCFO-1233xf may be separated by freezing out or "cold-trapping" HCFC-244bb preferentially over HCFO-1233xf and subsequently recovering a purer HCFC-244bb stream. More specifically, the temperature of the composition may be lowered to be below the freezing point of one of HCFC-244bb and HCFO-1233xf, but above the freezing point of the other. In certain embodiments, the temperature is below the freezing point of HCFC-244bb, but above the freezing point of HCFO-1233xf. Such a temperature may be between about −85° C. and about −75° C., in further embodiments between about −81° C. to about −78° C. As a result, HCFC-244bb is provided in a solid form, while HCFO-1233xf is provided in a liquid form. The solid HCFC-244bb can be recovered by standard means, such as, decantation, filtration, centrifugation, or the like.

In further embodiments, HCFO-1233xf may be removed using a solid adsorbent selected from activated carbons and zeolites and/or molecular sieves. More specifically, the mixture of HCFO-1233xf and HCFC-244bb (as a liquid or vapor phase) may be passed over a fixed bed of solid adsorbents selected from activated carbons and zeolites and/or molecular sieves, wherein the said zeolites and/or molecular sieves have a pore size adapted to selectively filter HCFO-1233xf from HCFO-244bb. In an embodiment, the pore diameter may be within a range of about 3 Å to about 10 Å, in further embodiments between about 3 Å to about 5 Å. Embodiments of such molecular sieves include, but are not limited to Type 5A and Type 13X molecular sieves, such as those produced by UOP, LLC. Also useful are 5A synthetic zeolites and the naturally derived zeolite, calcium chabazite. The foregoing is not necessary limiting to the invention. To this end, any molecular sieves and/or zeolites adapted or adaptable to selectively filter HCFO-1233xf from HCFC-244bb may be used in accordance with the present invention. Examples of the methods in which such molecular sieves and/or zeolites may be used in the present invention are provided in U.S. Pat. No. 4,906,796, the contents of which are incorporated herein by reference.

In even further embodiments, HCFO-1233xf may be separated from HCFC-244bb by standard chromatography. To this end, the feed mixture of HCFO-1233xf and HCFC-244bb is contacted with a bed containing stationary chromatographic substrate at conditions to effect the selective retention of one of the components by said substrate and recovering a substantially pure other component. As an example, 5% Fluocol phase on a 60/80 Carbopack B support can be used as such a stationary substrate. Examples of such techniques may be found in U.S. Pat. No. 3,903,187, the contents of which are incorporated herein by reference.

In another embodiment of the present invention, liquid hydrofluoric acid is added to a composition comprised of 2-chloro-1,1,1,2-tetrafluoropropane and 2-chloro-3,3,3-trifluoropropene. The composition may be the product obtained from the second fluorination process described hereinabove. The concentration thereof, in an embodiment, is greater than about 0.01% by weight and less than about 20% by weight and in another embodiment, the concentration ranges from about 0.05% to about 10% by weight and in another embodiment, the concentration of hydrofluoric acid is less than about 5% by weight. The HCFC-244bb utilized may come from or is part of the reactor effluent from the preceding step. Alternatively, it may be introduced from another source. The amount added is sufficient to form a mixture, which can separate out the 2-chloro-1,1,1,2-tetrafluoropropane and to form a product which is substantially free of 2-chloro-3,3,3-trifluoropropene and which is purer in the 2-chloro-1,1,1,2-tetrafluoropropane than the resulting mixture. In an embodiment, the resulting mixture is not a ternary azeotrope or ternary azeotropic-like composition. In a further embodiment, the HF is present in the mixture in an amount HF that is less than the amount required for forming a ternary azeotrope or azeotropic-like composition. In another embodiment, the resulting mixture forms a ternary azeotrope or ternary azeotropic-like composition. The amount of HF present in the mixture is less than 10 wt % of the mixture. In another embodiment, it is present in less than about 5 wt % of the mixture. In still further embodiment, the amount of is present is less than 3 wt % of the mixture. The resulting composition is distilled and the product substantially free of 2-chloro-3,3,3-trifluoropropene is collected. In an embodiment, a reboiler in communication with a plate or trayed tower is utilized. In this embodiment, an assembly comprised of a condenser and a trayed column is employed with a reboiler having the temperature control means typically used in a reboiler. The tower is a vertical assembly of plates or trays, on each of which vapor and liquid are contacted. The hydrofluorinated solution of the 2-chloro-1,1,1,2-tetrafluoropropane and 2-chloro-3,3,3-trifluoropropene is fed into a feed that leads into the plate tower. Typically, the feed is located around the middle of the plate tower. The liquid flows down the tower under the force of gravity, while the vapor flows upward under the force of a slight pressure drop from plate to plate. The highest pressure, however, is produced by the boiling in the reboiler, which is a heater located at the bottom in communication with the plate tower. The vapor passes through openings in each plate and contacts the liquid flowing across the plate. The reboiler portion of the column is utilized to remove the composition in a reboiler stream. comprised of 2-chloro-1,1,1,2-tetrafluoropropane that is substantially free of 2-chloro-3,3,3-trifluoropropene and the column is operated to remove in an overhead stream a composition comprised of a mixture of the 2-chloro-3,3,3-trifluoropropene in greater concentration than in the reboiler portion and some 2-chloro-1,1,1,2-tetrafluoropropane. Typical reflux condenser connected to the upper portion of the plate tower is employed to return a portion of the latter composition (i.e., the overhead portion) to the plate tower for further distillation, and separation. As the distillation is maintained, the fraction comprised of the purer 2-chloro-1,1,1,2-tetrafluoropropane substantially free of the 2-chloro-3,3,3-trifluoropropene is continually removed from the reboiler stream.

As noted above, the foregoing separation techniques may be used alone or in any combination to provide a composition of HCFC-244bb that is substantially free of HCFO-1233xf. To this end, the separation techniques may be performed alone or in any combination to result in a compositions having less than about 20.0 wt %, less than about 15.0 wt %, less than about 10.0 wt %, less than about 8.0 wt %, less than about 5.0 wt %, less than about 2.5 wt %, or less than about 1.0 wt % HCFO-1233xf. In other non-limiting embodiments, the techniques may be performed to provide a composition that is completely free of HCFO-1233xf, or a composition where no amount of HCFO-1233xf is detectable using standard detection means. For example, in one non-limiting embodiment, the mixture may be treated with a combination of azeotropic distillation followed by photochlorination followed by molecular sieves/zeolites to lower the level of HCFO-1233xf and result in a composition that is free or substantially free of HCFO-1233xf. Such a combination, however, is not limiting to the invention and may be adapted to incorporate one or more of any of the techniques provided herein or otherwise to achieve the desired level of HCFO-1233xf.

As described hereinabove, the present invention also provides 2-chloro-1,1,1,2-tetrafluoropropane that is substantially free of 3,3,3-trifluoropropyne. Thus, an embodiment of the present invention is directed to the process of preparing 2,3,3,3-tetrafluoropropene that is substantially free of 3,3,3-trifluoropropyne comprising:

(i) providing a starting composition comprising a 2-chloro-1,1,1,2-tetrafluoropropane that is substantially free of 2-chloro-3,3,3-trifluoropropene; and (ii) contacting said starting composition with a dehydrochlorination catalyst to produce a final composition comprising 2,3,3,3-tetrafluoropropene, said final composition being substantially free of 3,3,3-trifluoropropyne.

Another aspect of the present invention is directed to a process for producing 2,3,3,3-tetrafluoropropene that is substantially free of 3,3,3-trifluoropropyne comprising:

(i) providing a starting composition including a compound of Formulae I, II, or III:

wherein X is independently selected from F, Cl, Br, and I, provided that at least one X is not fluorine;

(ii) contacting the starting composition with a first fluorinating agent to produce a first intermediate composition including 2-chloro-3,3,3-trifluoropropene and a first chlorine-containing byproduct;

(iii) contacting the first intermediate composition with a second fluorinating agent to produce a second intermediate composition including 2-chloro-1,1,1,2-tetrafluoropropane and 2-chloro-3,3,3-trifluoropropene;

(iv) reducing the level of 2-chloro-3,3,3-trifluoropropene in the second intermediate composition to produce a third intermediate composition including 2-chloro-1,1,1,2-tetrafluoropropane and is substantially free of 2-chloro-3,3,3-trifluoropropene; and (v) dehydrochlorinating at least a portion of the 2-chloro-1,1,1,2-tetrafluoropropane to produce a reaction product including 2,3,3,3-tetrafluoropropene, said reaction product being substantially free of 3,3,3-trifluoropropyne.

In an embodiment, the 2,3,3,3-tetrafluoropropene that is formed is substantially free of 3,3,3-trifluoropropyne. For example, the 2,3,3,3-tetrafluoropropene that is formed as the product from these reactions contains less than about 0.1 wt % of 3,3,3-trifluoropropyne. In another embodiment the concentration of 3,3,3-trifluoro-propyne present with the 2,3,3,3-tetrafluoropropene contains less than 0.01 wt % of 3,3,3-trifluoropropyne at in another embodiment less than about 0.005% by weight. The amount of 3,3,3-trifluoropropyne present with the 2,3,3,3-tetrafluoropropene can be measured by techniques known in the art, such as by gas chromatography.

The following are examples of the invention and are not to be construed as limiting.

EXAMPLES

Example 1

This example illustrates how the HCFO-1233xf concentration in HCFC-244bb feed affects the conversion of HCFC-244bb during the continuous vapor phase dehydrochlorination reaction of HCFC-244bb to HFO-1234yf. A cylindrical Inconel 625 reactor of ¾" diameter immersed into a 3-zone electrical furnace was used. Process temperatures were recorded using a multi-point thermocouple placed inside the reactor. HCFC-244bb feed was fed into the bottom of the vertically mounted reactor and was vaporized before reaching reaction zone. The reaction was conducted under conditions of 480° C., 25 psig, and 12 g-organic/h. Effluent gases were passed through a gas sampling tube so that the progress of the reaction was monitored periodically via GC analysis of the contents of the gas sampling tube. As shown in Table 1, with decreasing HCFO-1233xf concentration in HCFC-244bb feed from 8.1 to 1.6 GC area %, the conversion of HCFC-244bb was notable increased.

TABLE 1

| 1233xf GC area % in feed | 244bb conversion, % |
|---|---|
| 20.0 | 21.0 |
| 14.0 | 21.6 |
| 8.1 | 21.6 |
| 4.6 | 28.3 |
| 1.6 | 36.4 |

Example 2

Figure 1:
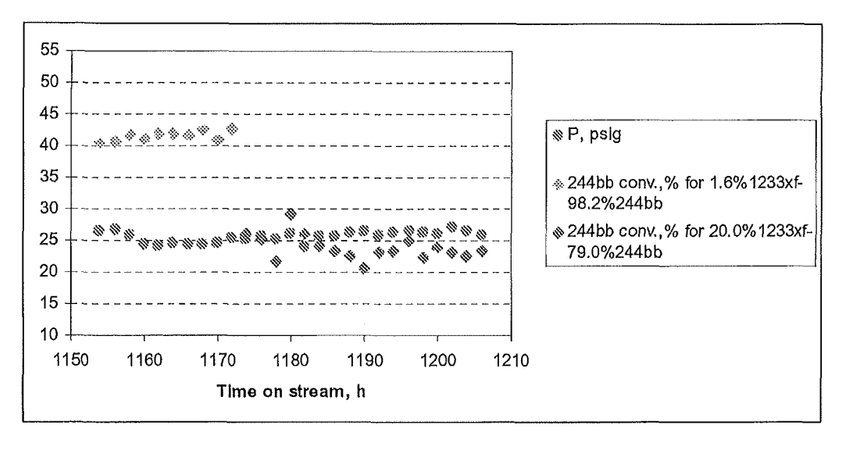
FIG. 1 illustrates the effects of HCFO-1233xf concentration with the conversion of HCFC-244bb to HFO-1234yf with pressure versus time in a gas phase reaction in a reaction vessel consisting of austenitic nickel-based material (particularly Inconel 625).

This example illustrates how the HCFO-1233xf concentration in HCFC-244bb feed affects the conversion of HCFC-244bb during the continuous vapor phase dehydrochlorination reaction of HCFC-244bb to HFO-1234yf. A cylindrical Inconel 625 reactor of ¾" diameter immersed into a 3-zone electrical furnace was used. Process temperatures were recorded using a multi-point thermocouple placed inside the reactor. HCFC-244bb feed was fed into the bottom of the vertically mounted reactor and was vaporized before reaching reaction zone. The reaction was conducted under conditions of 480° C., ~25 psig, and 12 g-organic/h. Effluent gases were passed through a gas sampling tube so that the progress of the reaction was monitored periodically via GC analysis of the contents of the gas sampling tube. As shown in FIG. 1, with increasing HCFO-1233xf concentration in HCFC-244bb feed from 1.6 to 20 GC area %, the conversion of HCFC-244bb was notable decreased from above 40% to below 25%.

Example 3

This example illustrates how the HCFO-1233xf concentration in HCFC-244bb feed affects the amount of $CF_3CCH$ formed during the continuous vapor phase dehydrochlorination reaction of HCFC-244bb to HFO-1234yf. A U-shaped Inconel 625 reactor of 1" diameter immersed into a S and Bath furnace was used. Process temperatures were recorded using a multi-point thermocouple placed inside the reactor. HCFC-244bb feed was fed into the bottom of the vertically mounted vaporizer and was vaporized before reaching reaction zone. The reaction was conducted under conditions of 480° C., 50 psig, and 1 lb-organic/h. Effluent gases were periodically sampled for GC analysis so that the progress of the reaction was monitored. As shown in Table 2, with decreasing 1233xf concentration in 244bb feed from 10.0 to 3.0 GC area %, the amount of $CF_3CCH$ formed and the mole ratio of $CF_3CCH$/1234yf in reactor effluent were notably decreased.

TABLE 2

| 1233xf GC area % in feed | $CF_3CCH$ concentration in reactor effluent, ppm | $CF_3CCH$/1234yf mole ratio × 1000 |
|---|---|---|
| 10.0 | 409 | 2.69 |
| 7.6 | 368 | 1.92 |
| 3.0 | 258 | 0.87 |

106 lbs of 3% HF/92.15%244bb/4.85%1233xf was charged into reboiler. Batch distillation was started at 40 psig. Samples were periodically taken from column overhead and reboiler and analyzed by GC for organic compositions and by acid-base titration for HF concentrations. Continuous distillation was initiated after 244bb concentration in the reboiler reached about 98 GC area % (or 1233xf was about 2 GC area %). The mixed feed comprising HF, 244bb, and 1233xf was continuously fed into column as a liquid form through a feeding port located in the middle of the column. The overhead stream was directed to a 10 wt % KOH aqueous solution for acid removal and then the organic was compressed and collected into a PCC (product collection cylinder) after being passed through a drying column. The reboiler stream was directly compressed and collected into another PCC. During the course of operation, the liquid level in reboiler was maintained at a constant level by keeping the sum of overhead takeoff rate and reboiler removal rate equal to the feed rate. As shown in Table 3, 1233xf was enriched in overhead stream but depleted in reboiler stream. As a result, 98 GC area % 244bb was obtained from the distillation. Analysis also indicated that almost all HF included in feed left distillation column from the overhead (in other words, no or little HF appeared in reboiler stream).

TABLE 3

| Time, h | Feed rate[1], lb/h | OH take-off rate, lb/h | Reboiler stream rate, lb/h | Composition at overhead stream, GC area % | | | | Composition at reboiler stream, GC area% | | | |
|---|---|---|---|---|---|---|---|---|---|---|---|
| | | | | 245cb | 244bb | 1233xf | others | 245cb | 244bb | 1233xf | others |
| 4 | 0.5 | 0.15 | 0.35 | 0.0349 | 92.1626 | 7.8025 | 0.0000 | | | | |
| 8 | 0.5 | 0.15 | 0.35 | 0.0102 | 92.5472 | 7.4335 | 0.0091 | | | | |
| 12 | 0.5 | 0.15 | 0.35 | | 92.5188 | 7.2292 | 0.2520 | | 98.0218 | 1.9630 | 0.0152 |
| 16 | 0.5 | 0.15 | 0.35 | 0.0063 | 91.9291 | 8.0579 | 0.0067 | | | | |
| 20 | 0.5 | 0.15 | 0.35 | 0.0075 | 91.8093 | 8.1832 | 0.0000 | | | | |

[1]Feed composition: 3 wt % HF/97 wt % organic (0.0029% 245cb, 94.9636% 244bb, and 5.0335% 1233xf)

Example 4

This example illustrates how the addition of HF into a mixture of 244bb and 1233xf helps remove 1233xf in subsequent distillation. The distillation column used consisted of a 10 gallon reboiler, 2 inch ID by 8 feet Propack column, and a 5 ft$^2$ shell and tube condenser. The column was packed with Monel ¼" Pro-Pack dump packing and had about 30-35 theoretical plates. The distillation column was equipped with temperature, pressure, and differential pressure transmitters.

Example 5

This distillation was conducted as in Example 4, using in the same distillation column except that a feed containing only about 400 ppm of liquid HF was used. As shown in Table 4, with the presence of HF at just hundreds of ppm the 1233xf concentrations in the overhead takeoff stream were above 6 GC area % while they remained at around 2.5 GC area % in the reboiler drawoff stream, indicating the presence of HF even at just hundreds of ppm facilitates the separation of 1233xf from 244bb.

TABLE 4

| Time, h | Feed rate, lb/h | OH take-off rate, lb/h | Reboiler stream rate, lb/h | Composition at overhead stream, GC area % | | | | Composition at reboiler stream, GC area % | | | |
|---|---|---|---|---|---|---|---|---|---|---|---|
| | | | | 245cb | 244bb | 1233xf | others | 245cb | 244bb | 1233xf | others |
| 4 | 1.5 | 0.9 | 0.6 | | 93.6515 | 6.3485 | 0.0000 | | 97.5396 | 2.4604 | 0.0000 |
| 8 | 1.5 | 0.9 | 0.6 | | 93.6585 | 6.2925 | 0.0490 | | 97.5003 | 2.4997 | 0.0000 |
| 12 | 1.5 | 0.9 | 0.6 | | 94.2539 | 5.7461 | 0.0000 | | | | |
| 16 | 1.5 | 0.9 | 0.6 | | 93.9344 | 6.0656 | 0.0000 | | | | |
| 20 | 1.5 | 0.9 | 0.6 | | 93.7662 | 6.2338 | 0.0000 | | 97.4410 | 2.5434 | 0.0156 |
| 24 | 1.5 | 0.9 | 0.6 | | 93.8983 | 6.1017 | 0.0000 | | 97.4466 | 2.5534 | 0.0000 |
| 28 | 1.5 | 0.9 | 0.6 | | 93.7186 | 6.2814 | 0.0000 | | 97.4543 | 2.5457 | 0.0000 |
| 32 | 1.5 | 0.9 | 0.6 | | 93.8642 | 6.1358 | 0.0000 | | 97.4230 | 2.5770 | 0.0000 |
| 36 | 1.5 | 0.9 | 0.6 | | 93.8747 | 6.1253 | 0.0000 | | | | |
| 40 | 1.5 | 0.9 | 0.6 | | 93.6065 | 6.3935 | 0.0000 | | | | |

TABLE 4-continued

| Time, h | Feed rate, lb/h | OH take-off rate, lb/h | Reboiler stream rate, lb/h | Composition at overhead stream, GC area % | | | | Composition at reboiler stream, GC area % | | | |
|---|---|---|---|---|---|---|---|---|---|---|---|
| | | | | 245cb | 244bb | 1233xf | others | 245cb | 244bb | 1233xf | others |
| 44 | 1.5 | 0.9 | 0.6 | | 93.7067 | 6.2933 | 0.0000 | | 97.4151 | 2.5849 | 0.0000 |
| 48 | 1.5 | 0.9 | 0.6 | | 93.7888 | 6.2112 | 0.0000 | | 97.3860 | 2.614 | 0.0000 |
| 52 | 1.5 | 0.9 | 0.6 | | 93.8067 | 6.1933 | 0.0000 | | | | |
| 56 | 1.5 | 0.9 | 0.6 | | 93.6921 | 6.3041 | 0.0038 | | | | |
| 60 | 1.5 | 0.9 | 0.6 | | 93.7278 | 6.2722 | 0.0000 | | 97.3845 | 2.6155 | 0.0000 |

[1]Feed composition: ~400 ppm HF/~99.96 wt % organic (94.9376% 244bb, and 5.0554% 1233xf)

The 244bb thus obtained is next dehydrochlorinated in accordance with the procedure described herein to produce HFO-1234yf.

Example 6

3,3,3-Trifluoropropyne formation increased with increase of 1233xf concentration in 244bb at 480 C 244bb containing different amounts of 1233xf was passed through a ½"×12" (ID 0.334") Inconel 625 tube for dehydrochlorination at 1.2 ml liquid per hour feed rate at 480° C. The stream from the reactor was analyzed by GC and GC-MS. The result of the test is listed in Table below. The result shows formation of 3,3,3-trifluoropropyne increased with increase of 1233xf concentration.

TABLE 5

| | 3, 3, 3-trifluoropropyne | |
|---|---|---|
| Sample | Staring material GC area % | After reaction |
| 1% 1233xf in 244bb | 0.003 | 0.049 |
| 5% 1233xf in 244bb | ND | 0.047 |
| 9% 1233xf in 244bb | ND | 0.079 |
| 97.5% 1233xf | ND | 0.778 |

Example 7

3,3,3-Trifluoropropyne formation increased with increase of 1233xf concentration in 244bb at 460° C.

244bb contains different level of 1233xf was passed through a ½"×12" (ID 0.334") Inconel 625 tube for dehydrochlorination at 1.2 ml liquid per hour feed rate at 460 C. The stream from the reactor was analyzed by GC and GC-MS. The result of the test is listed in Table below. The result shows formation of 3,3,3-trifluoropropyne increased with increase of 1233xf concentration.

TABLE 6

| | 3,3,3-trifluoropropyne | |
|---|---|---|
| Sample | Staring material GC area% | After reaction |
| 1% 1233xf in 244bb | 0.003 | 0.003 |
| 5% 1233xf in 244bb | ND | 0.016 |
| 9% 1233xf in 244bb | ND | 0.032 |

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A process for reducing the concentration of 2-chloro-3,3,3-trifluoropropene in a composition comprised of 2-chloro-1,1,1,2-tetrafluoropropane and 2-chloro-3,3,3-trifluoropropene which comprises conducting a process selected from
    (a) photochlorinating the composition to form 1,2,2-trichloro-3,3,3-trifluoropropane in the presence of at least one chlorination agent and separating the 2-chloro-1,1,1,2-tetrafluoropropane from the 1,2,2-trichloro-3,3,3-trifluoropropane;
    (b) passing the composition over a fixed bed of solid adsorbents selected from activated carbons and zeolites or molecular sieves, and collecting the 2-chloro-1,1,1,2-tetrafluoropropane from the fixed bed of solid adsorbents; and
    (c) mixing said composition with liquid hydrofluoric acid to form a mixture comprised of 2-chloro-1,1,1,2-tetrafluoropropane and 2-chloro-3,3,3-trifluoropropene and HF, said HF present in the mixture is less than about 10% by weight; distilling the mixture and collecting the distilled product substantially free of 2-chloro-3,3,3-trichloropropene and purer in 2-chloro-1,1,1,2-tetrafluoropropane.

2. The process according to claim 1 where the composition is photochlorinated.

3. The process according to claim 2 where photochlorinating comprises exposing the composition to radiation in the presence of said at least one chlorination agent.

4. The process according to claim 1 wherein the photochlorinating is carried out in the vapor phase at a temperature ranging from about −20 C to about 200 C.

5. The process according to claim 1 wherein 2-chloro-1,1,1,2-tetrafluoropropane is separated from 2-chloro-3,3,-trifluoropropene utilizing activated carbon.

6. The process according to claim 1 wherein 2-chloro-1,1,1,2-tetrafluoropropane is separated from 2-chloro-3,3,-trifluoropropene utilizing molecular sieves or zeolites.

7. The process according to claim 6 wherein the pores of the molecular sieves or zeolites ranges from about 3 Angstroms to about 10 Angstroms.

8. The process according to claim 1 comprising mixing said composition with liquid hydrofluoric acid to form a mixture comprised of 2-chloro-1,1,1,2-tetrafluoropropane and 2-chloro-3,3,3-trifluoropropene and HF, said HF is present in the mixture in less than about 10% by weight; and distilling the mixture; and collecting the distilled product substantially free of 2-chloro-3,3,3-trichloropropene and purer in 2-chloro-1,1,1,2-tetrafluoropropane.

9. A process for preparing 2,3,3,3-tetrafluoropropene comprising:
(i) subjecting a first composition comprising a 2-chloro-1,1,1,2-tetrafluoropropane and 2-chloro-3,3,3-trifluoropropene to purification process that reduces the concentration of 2-chloro-3,3,3-trifluoropropene so that the composition is substantially free of 2-chloro-3,3,3-trifluoropropene; and
(ii) contacting said purified composition with a dehydrochlorination catalyst to produce a final composition comprising 2,3,3,3-tetrafluoropropene, wherein said purification process is selected from
(a) photochlorinating the first composition to form 1,2,2-trichloro-3,3,3-trifluoropropane in the presence of at least one chlorination agent and separating the 2-chloro-1,1,1,2-tetrafluoropropane from the 1,2,2-trichloro-3,3,3-trifluoropropane;
(b) passing the first composition over a fixed bed of solid adsorbents selected from activated carbon and zeolites or molecular sieves, and collecting the 2-chloro-1,1,1,2-tetrafluoropropane from the of activated carbon, zeolites or molecular sieves; and
(c) mixing said first composition with liquid hydrofluoric acid to form a mixture comprised of 2 chloro-1,1,1,2-tetrafluoropropane and 2-chloro-3,3,3-trifluoropropene and HF, said HF present in the mixture is less than about 10% by weight; and feeding the mixture and collecting the distilled product substantially free of 2-chloro-3,3,3-trichloropropene and purer in 2-chloro-1,1,1,2-tetrafluoropropane.

10. A process for preparing 2,3,3,3-tetrafluoropropene comprising:
(i) providing a first composition including a compound of Formulae I, II, or III:

$CX_2=CCl-CH_2X$ (I);

$CX_3-CCl=CH_2$ (II); or $CX_3-CHCl-CH_2X$ (III)

wherein X is independently selected from F, Cl, Br, and I, provided that at least one X is not fluorine;
(ii) contacting the first composition with a first fluorinating agent to produce a first intermediate composition including 2-chloro-3,3,3-trifluoropropene and a first chlorine-containing byproduct;
(iii) contacting the first intermediate composition with a second fluorinating agent to produce a second intermediate composition including 2-chloro-1,1,1,2-tetrafluoropropane and 2-chloro-3,3,3-trifluoropropene;
(iv) reducing the concentration of 2-chloro-3,3,3-trifluoropropene in the second intermediate composition to produce a third intermediate composition comprising 2-chloro-1,1,1,2-tetrafluoropropane that is substantially free of 2-chloro-3,3,3-trifluoropropene; and
(v) dehydrochlorinating at least a portion of the third intermediate composition comprising 2-chloro-1,1,1,2-tetrafluoropropane to produce a reaction product including 2,3,3,3-tetrafluoropropene, wherein the second intermediate composition comprised of 2-chloro-1,1,1,2-tetrafluoropropene is made substantially free of 2-chloro-3,3,3-trifluoropropene by subjecting the second intermediate composition to a process selected from
(a) photochlorinating the second intermediate composition to form 1,2,2,-trichloro-3,3,3-trifluoropropane in the presence of at least one chlorination agent and separating the 2-chloro-1,1,1,2-tetrafluoropropane from the 1,2,2,-trichloro-3,3,3-trifluoropropane;
(b) passing the second intermediate composition over a fixed bed of solid adsorbents selected from activated carbons and zeolites or molecular sieves and collecting the 2-chloro-1,1,1,2-tetrafluoropropane from the activated carbon, zeolites or molecular sieves; and
(c) mixing said second intermediate composition with liquid hydrofluoric acid to form a mixture comprised of 2-chloro-1,1,1,2-tetrafluoropropane and 2-chloro-3,3,3-trifluoropropene and HF, said HF present in the mixture is less than about 10% by weight; distilling the mixture; and collecting the distilled product substantially free of 2-chloro-3,3,3-trichloropropene and purer in 2-chloro-1,1,1,2-tetrafluoropropane.

11. The process according to claim 9 wherein the third intermediate composition comprises 2-chloro-3,3,3-trifluoropropene in an amount less than about 20 wt %.

12. The process according to claim 10 wherein the third intermediate composition comprises 2-chloro-3,3,3-trifluoropropene in an amount less than about 5 wt %.

13. A process of preparing 2,3,3,3-tetrafluoropropene that is substantially free of 3,3,3-trifluoropropyne comprising:
(i) Providing a first composition comprising a 2-chloro-1,1,1,2-tetrafluoropropane that is substantially free of 2-chloro-3,3,3-trifluoropropene; and
(ii) contacting said first composition with a dehydrochlorination catalyst to produce a final composition comprising 2,3,3,3-tetrafluoropropene, said final composition being substantially free of 3,3,3-trifluoropropyne.

14. A process for producing 2,3,3,3-tetrafluoropropene that is substantially free of 3,3,3-trifluoropropyne comprising:
(i) providing a first composition including a compound of Formulae I, II, or III:

$CX_2=CCl-CH_2X$ (I);

$CX_3-CCl=CH_2$ (II); or $CX_3-CHCl-CH_2X$ (III)

wherein X is independently selected from F, Cl, Br, and I, provided that at least one X is not fluorine;
(ii) contacting the first composition with a first fluorinating agent to produce a first intermediate composition including 2-chloro-3,3,3-trifluoropropene and a first chlorine-containing byproduct;
(iii) contacting the first intermediate composition with a second fluorinating agent to produce a second intermediate composition including 2-chloro-1,1,1,2-tetrafluoropropane and 2-chloro-3,3,3-trifluoropropene;
(iv) reducing the level of 2-chloro-3,3,3-trifluoropropene in the second intermediate composition to produce a third intermediate composition including 2-chloro-1,1,1,2-tetrafluoropropane that is substantially free of 2-chloro-3,3,3-trifluoropropene; and
(v) dehydrochlorinating at least a portion of the third intermediate composition comprised of 2-chloro-1,1,1,2-tetrafluoropropane to produce a reaction product including 2,3,3,3-tetrafluoropropene, said reaction product being substantially free of 3,3,3-trifluoropropyne.

15. The process according to claim 13 where the amount of 3,3,3-trifluoropropyne present in the reaction product is less than 0.05 wt %.

16. The process according to claim 14 where the amount of 3,3,3-trifluoropropyne present in the reaction product is less than 0.05 wt %.

17. The process according to claim 13 wherein the first composition comprised of 2-chloro-1,1,1,2-tetrafluoropropane is made substantially free of 2-chloro-3,3,3-trifluoropropene by
- (a) photochlorinating the first composition to form 1,2,2-trichloro-3,3,3-trifluoropropane in the presence of at least one chlorination agent and separating the 2-chloro-1,1,1,2-tetrafluoropropane from the 1,2,2-trichloro-3,3,3-trifluoropropane;
- (b) passing the first composition over a fixed bed of solid adsorbents selected from activated carbons and zeolites or molecular sieves, and collecting the 2-chloro-1,1,1,2-tetrafluoropropane from the fixed bed of solid adsorbents;
- (c) mixing said first composition with liquid hydrofluoric acid to form a mixture comprised of 2-chloro1,1,1,2-tetrafluoropropane and 2-chloro-3,3,3-trifluoropropene and HF, said HF present in the mixture is less than about 10% by weight and distilling the mixture and collecting the distilled product substantially free of 2-chloro-3,3,3-trichloropropene and purer in 2-chloro-1,1,1,2-tetrafluoropropane than in said mixture.

18. The process according to claim 17 where the first composition is photochlorinated.

19. The process according to claim 18 where photochlorinating comprises exposing the starting composition to radiation in the presence of said at least one chlorination agent.

20. The process according to claim 17 wherein the photochlorinating is carried out in the vapor phase at a temperature ranging from about −20 C to about 200 C.

21. The process according to claim 17 wherein 2-chloro-1,1,1,2-tetrafluoropropane is separated from 2-chloro-3,3,3-trifluoropropene utilizing activated carbon.

22. The process according to claim 17 wherein 2-chloro-1,1,1,2-tetrafluoropropane is separated from 2-chloro-3,3,3-trifluoropropene utilizing molecular sieves or zeolites.

23. The process according to claim 22 wherein the pores of the molecular sieves or zeolites ranges from about 3 Angstroms to about 10 Angstroms.

24. The process according to claim 17 comprising mixing said first composition with liquid hydrofluoric acid to form a mixture comprised of 2-chloro-1,1,1,2-tetrafluoropropane and 2-chloro-3,3,3-trifluoropropene and HF, said HF is present in the mixture in less than about 10% by weight; distilling the mixture; and collecting the distilled product substantially free of 2-chloro-3,3,3-trichloropropene and purer in 2-chloro-1,1,1,2-tetrafluoropropane than in said first composition.

25. The process according to claim 13 wherein the first composition comprises 2-chloro-3,3,3-trifluoropropene in an amount less than about 20 wt %.

26. The process according to claim 13 wherein the first composition comprises 2-chloro-3,3,3-trifluoropropene in an amount less than about 5 wt %.

\* \* \* \* \*